United States Patent
Ono et al.

(10) Patent No.: US 7,809,430 B2
(45) Date of Patent: Oct. 5, 2010

(54) LEAK DETECTING APPARATUS

(75) Inventors: Seiichi Ono, Tokyo (JP); Masahiro Sakakibara, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 778 days.

(21) Appl. No.: 11/575,211

(22) PCT Filed: Sep. 13, 2005

(86) PCT No.: PCT/JP2005/016811
§ 371 (c)(1),
(2), (4) Date: Mar. 13, 2007

(87) PCT Pub. No.: WO2006/030764
PCT Pub. Date: Mar. 23, 2006

(65) Prior Publication Data
US 2007/0225637 A1 Sep. 27, 2007

(30) Foreign Application Priority Data
Sep. 14, 2004 (JP) .............................. 2004-267062

(51) Int. Cl.
*A61B 6/00* (2006.01)
(52) U.S. Cl. .................................................... 600/475
(58) Field of Classification Search .............. 73/861.05, 73/861.27, 597, 592; 600/407, 473, 475, 600/476, 479
See application file for complete search history.

(56) References Cited

U.S. PATENT DOCUMENTS
4,647,281 A * 3/1987 Carr ........................... 604/503
(Continued)

FOREIGN PATENT DOCUMENTS
EP 1 472 973 A1 11/2004
(Continued)

OTHER PUBLICATIONS
PCT Forms PCT/IB/338, PCT/IB/373, PCT/ISA/237 for PCT/JP2005/016811.

*Primary Examiner*—John Fitzgerald
(74) *Attorney, Agent, or Firm*—Knobbe Martens Olson & Bear LLP

(57) ABSTRACT

A leak detecting apparatus is provided which can detect leak of a liquid injected through an injection needle into a blood vessel of a human body near its surface with high accuracy. The apparatus emits a light ray in a predetermined wavelength band containing a particular wavelength at which the reflectivity for the liquid is lower than the reflectivity for internal tissues of the human body, to the human body at a position thereof where the injection needle is inserted, and detects the light ray in the wavelength band reflected inside the human body. The apparatus measures the average intensity of the detected light ray in the wavelength band and the intensity of the detected light ray at the particular wavelength to determine an occurrence of leak when the ratio of the intensity at the particular wavelength to the measured average intensity in the wavelength band is lower than a predetermined reference value. Variations in human body or physical condition affect the whole of the wavelength band but have no effects on the relative relationships between the wavelength band and the particular wavelength. Thus, the leak of the liquid can be detected without being affected by variations in human body or physical condition.

8 Claims, 12 Drawing Sheets

U.S. PATENT DOCUMENTS

| | | | |
|---|---|---|---|
| 4,877,034 A * | 10/1989 | Atkins et al. | 600/475 |
| 4,947,851 A * | 8/1990 | Sarvazyan et al. | 600/438 |
| 4,959,050 A * | 9/1990 | Bobo, Jr. | 604/505 |
| 5,255,564 A * | 10/1993 | Glad et al. | 73/597 |
| 5,255,683 A * | 10/1993 | Monaghan | 600/458 |
| 5,334,141 A * | 8/1994 | Carr et al. | 604/503 |
| 5,816,242 A * | 10/1998 | Cewers | 128/204.21 |
| 5,947,910 A | 9/1999 | Zimmet | |
| 5,954,668 A * | 9/1999 | Uber et al. | 600/549 |
| 5,964,703 A * | 10/1999 | Goodman et al. | 600/382 |
| 5,969,254 A * | 10/1999 | Yamaguchi | 73/602 |
| 6,375,624 B1 * | 4/2002 | Uber et al. | 600/549 |
| 6,408,204 B1 | 6/2002 | Hirschman | |
| 6,459,931 B1 * | 10/2002 | Hirschman | 600/547 |
| 6,487,428 B1 * | 11/2002 | Culver et al. | 600/310 |
| 7,047,058 B1 * | 5/2006 | Dvorsky et al. | 600/407 |
| 7,122,012 B2 * | 10/2006 | Bouton et al. | 600/587 |
| 7,546,776 B2 * | 6/2009 | Ono | 73/861.25 |
| 7,591,792 B2 * | 9/2009 | Bouton | 600/587 |
| 2002/0040193 A1 * | 4/2002 | Hirschman | 600/547 |
| 2002/0172323 A1 * | 11/2002 | Karellas et al. | 378/51 |
| 2003/0036674 A1 * | 2/2003 | Bouton | 600/12 |
| 2003/0036713 A1 * | 2/2003 | Bouton et al. | 600/587 |
| 2004/0225255 A1 * | 11/2004 | Ono | 604/65 |
| 2006/0178616 A1 * | 8/2006 | Hartman et al. | 604/65 |

FOREIGN PATENT DOCUMENTS

| | | |
|---|---|---|
| JP | 63-89170 | 4/1988 |
| JP | 2004-194802 A | 7/2004 |
| JP | 2005-152577 A | 6/2005 |
| JP | 2005-160857 A | 6/2005 |

* cited by examiner

[Fig. 1]
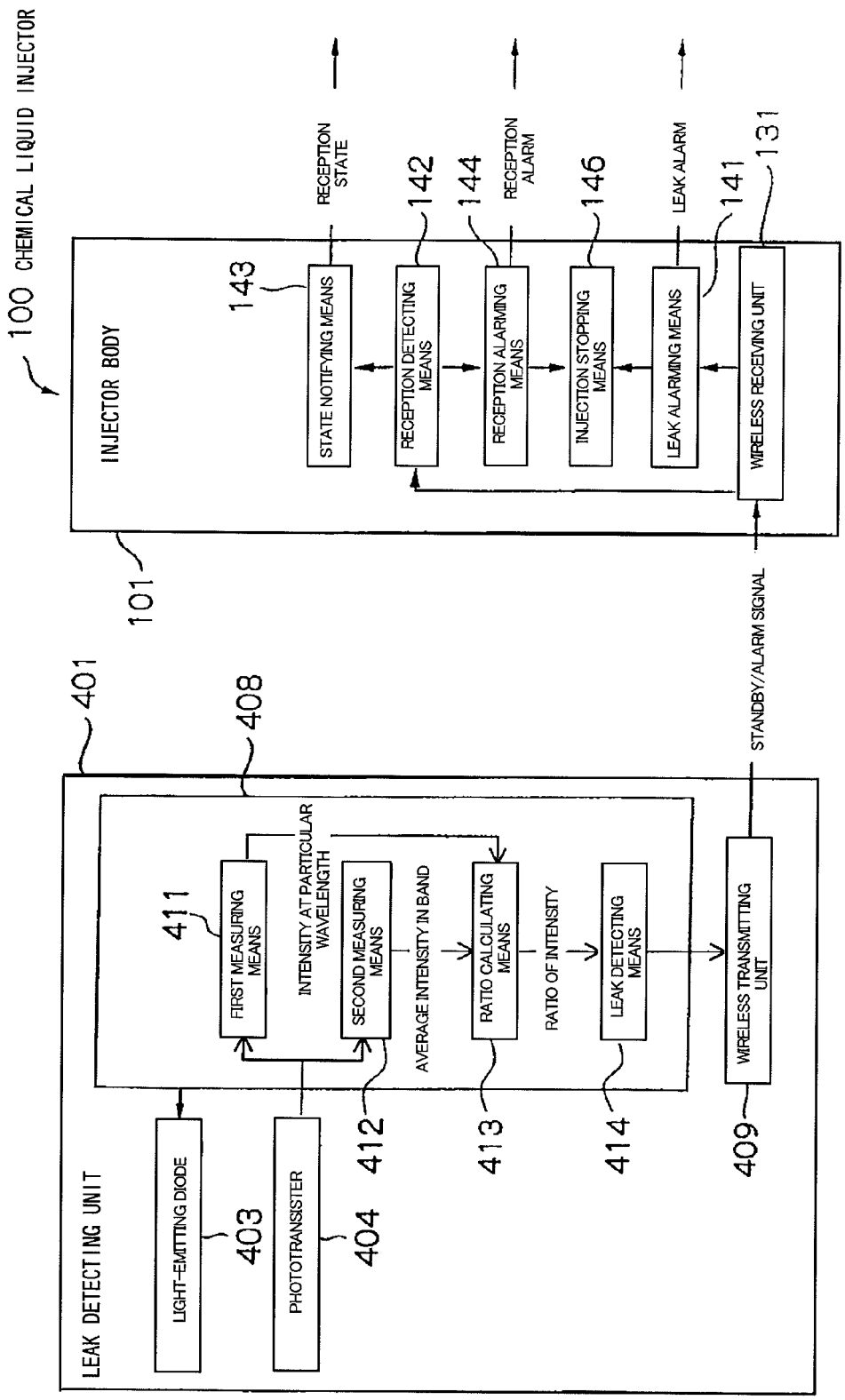

[Fig. 2]
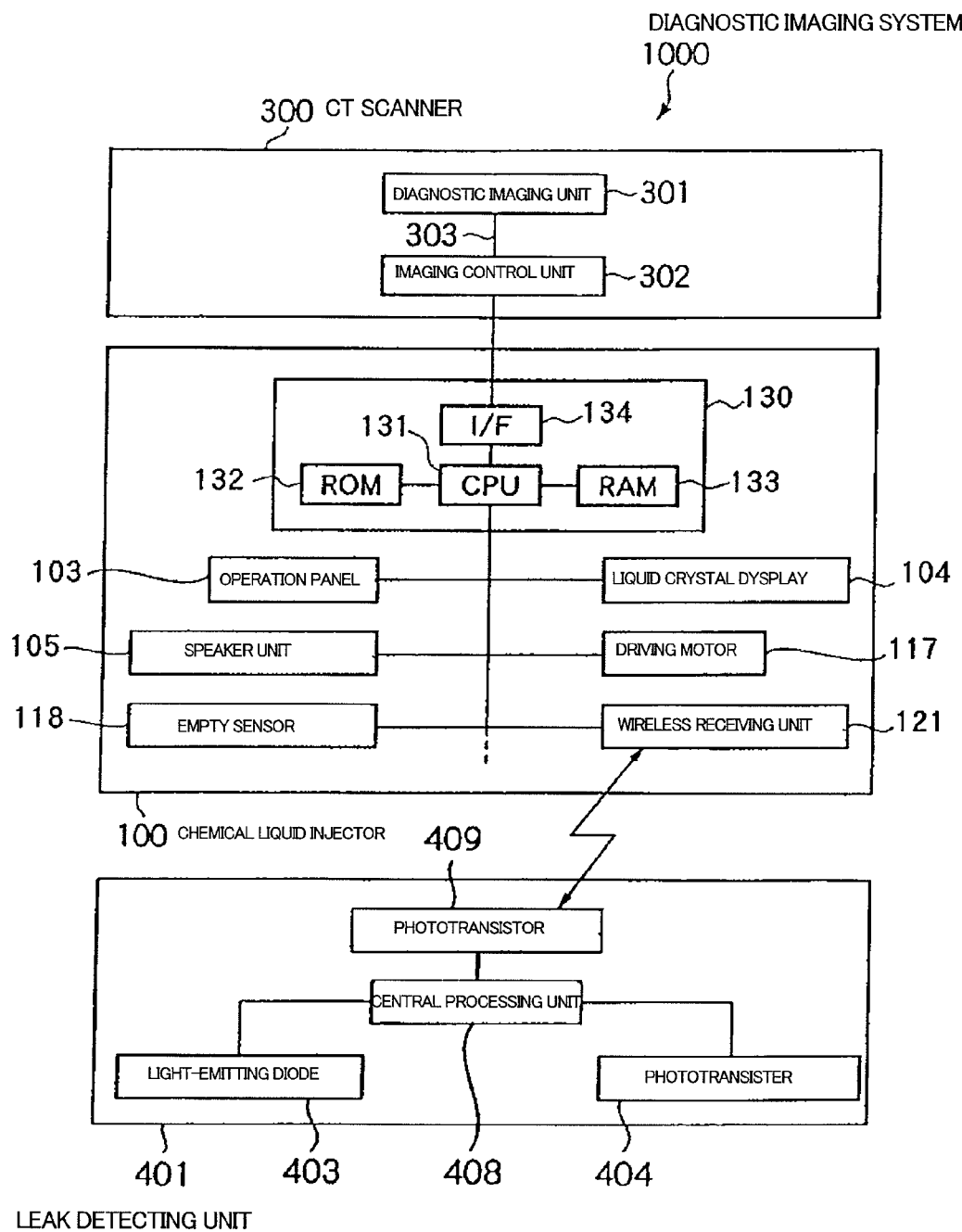

[Fig. 3]
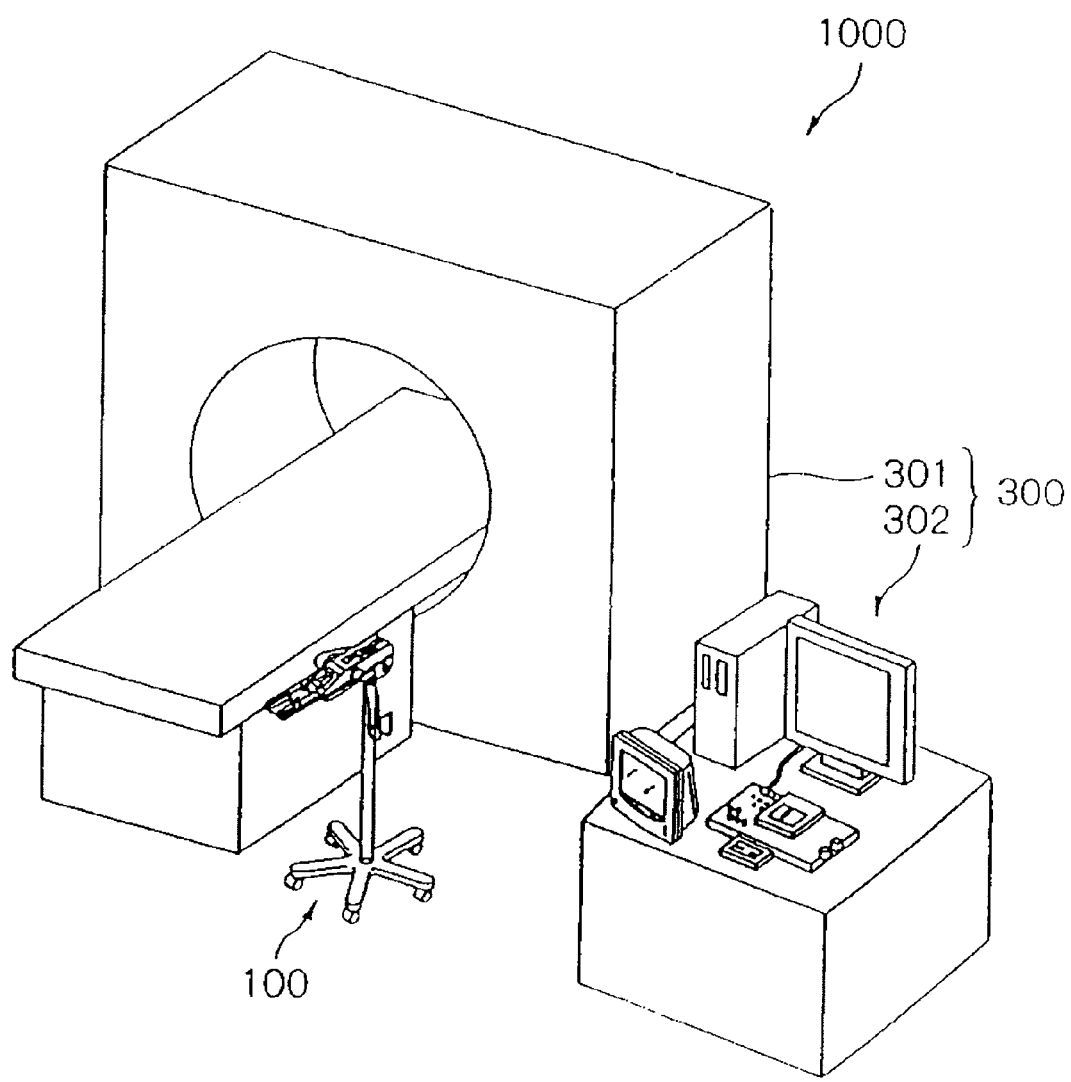

[Fig. 4]
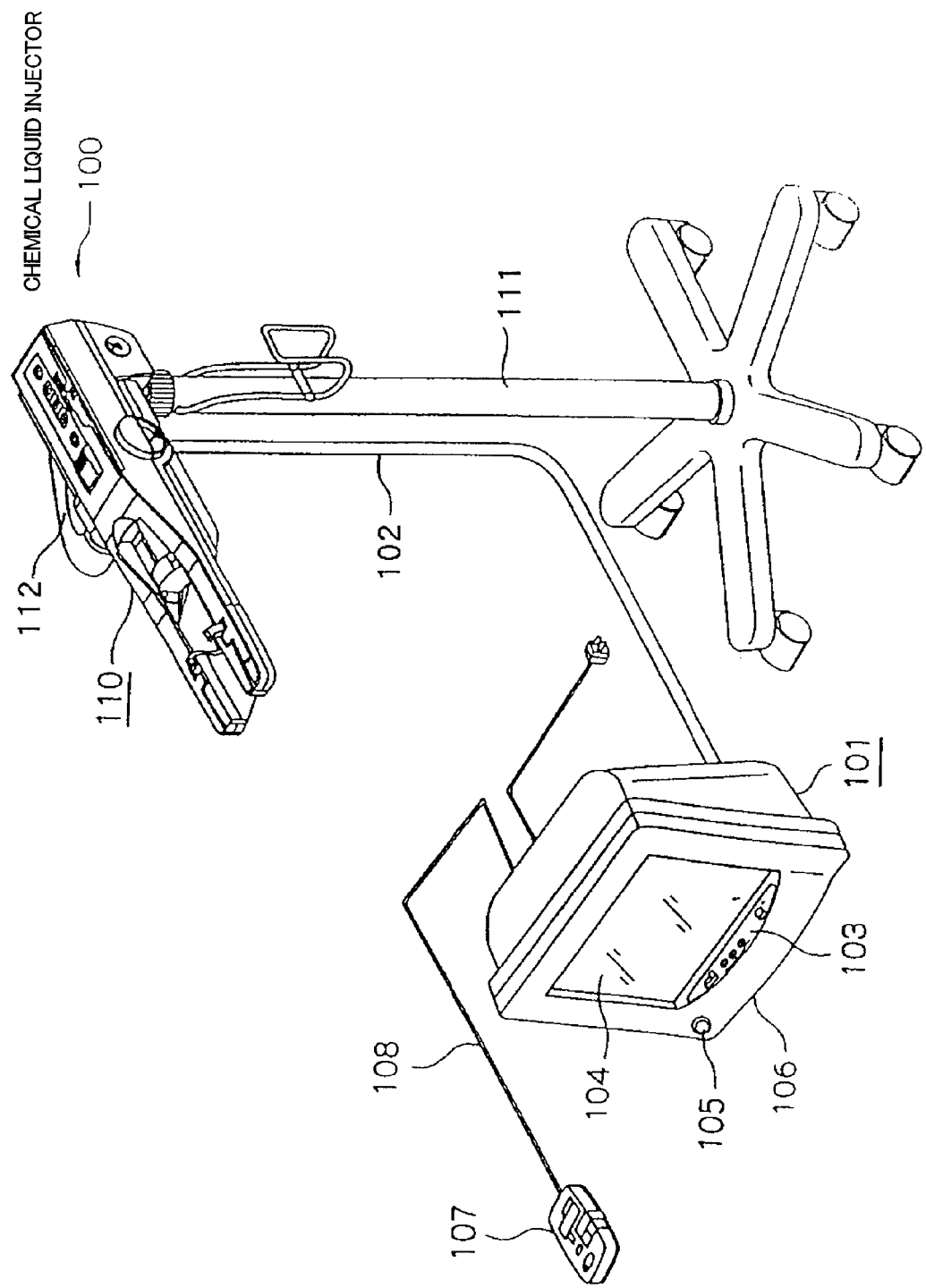

[Fig. 5]
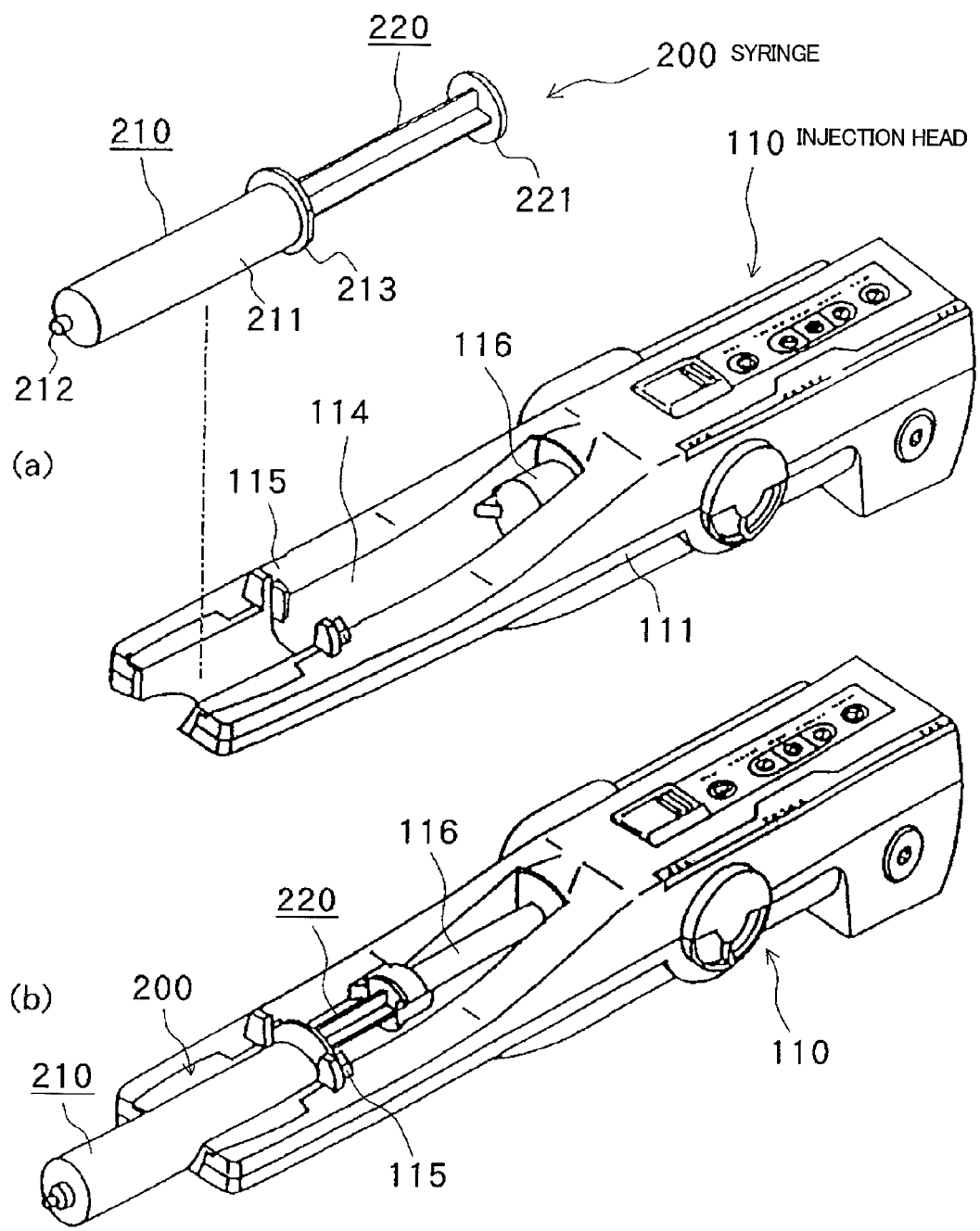

[Fig. 6]
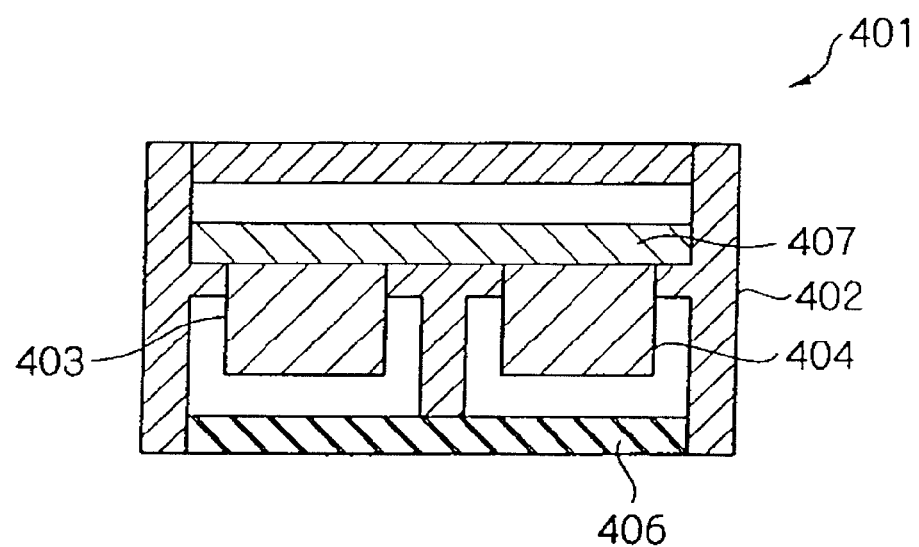

[Fig. 7]
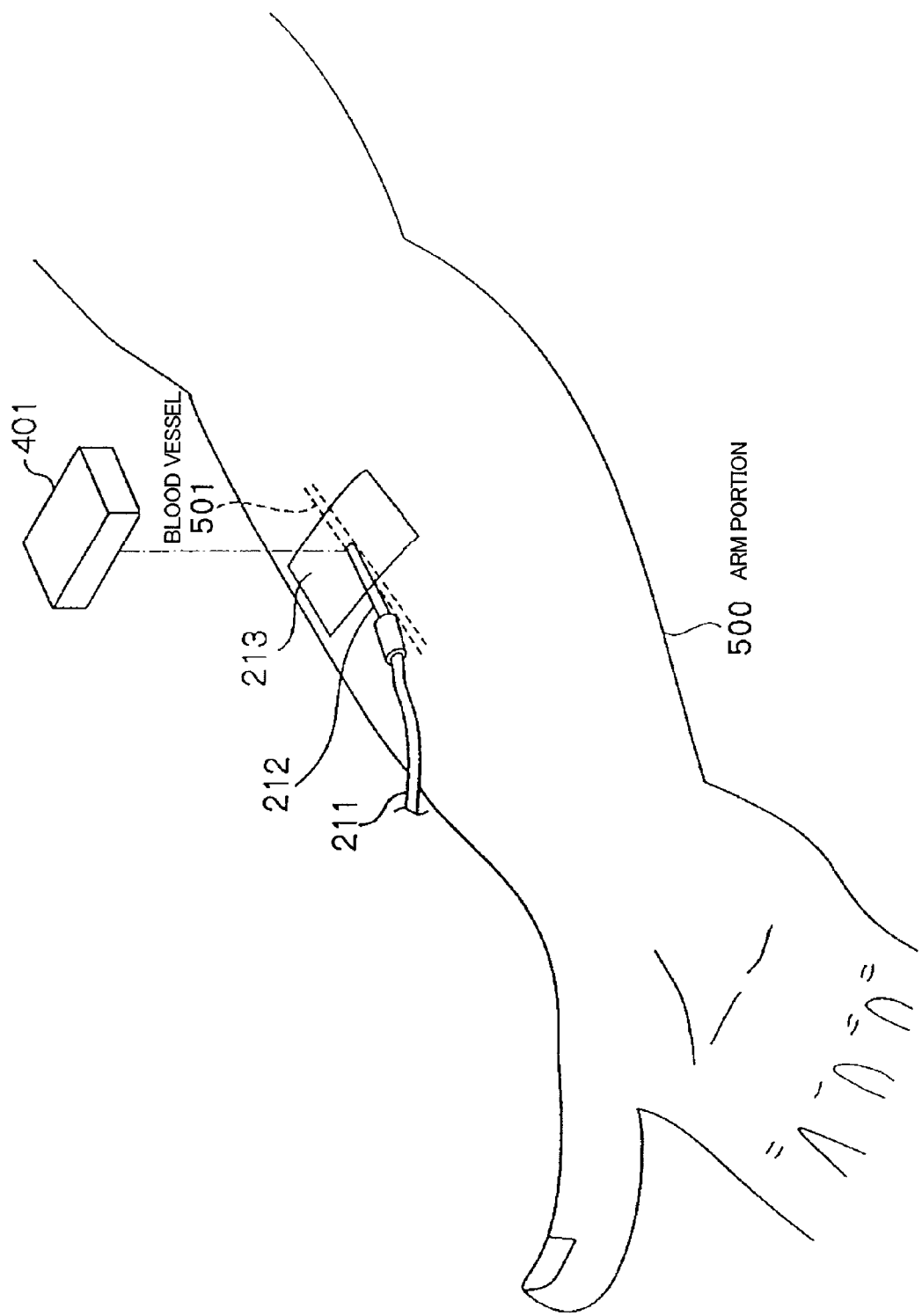

[Fig. 8]
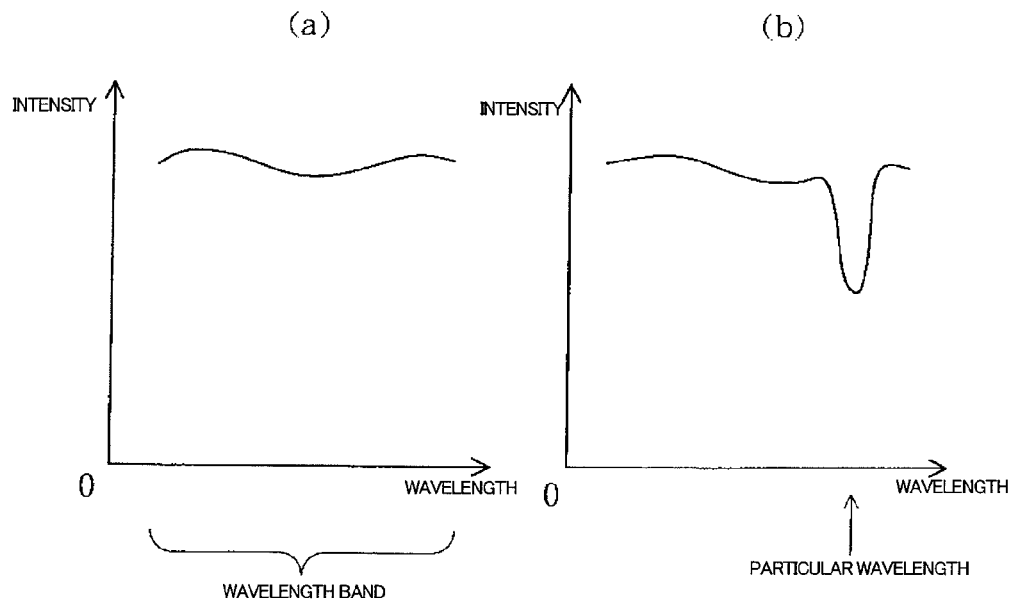
[Fig. 9]
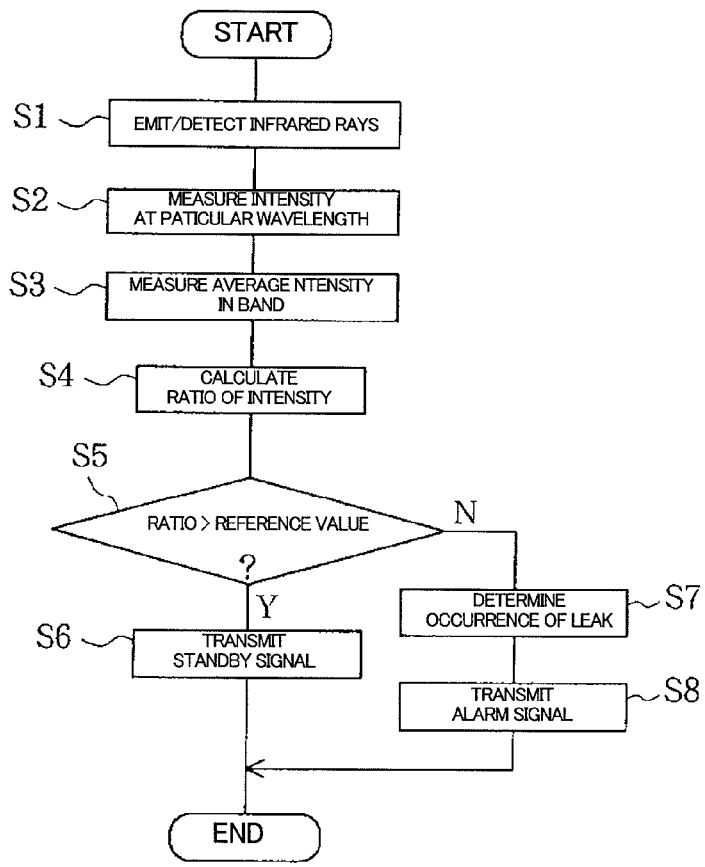

[Fig. 10]
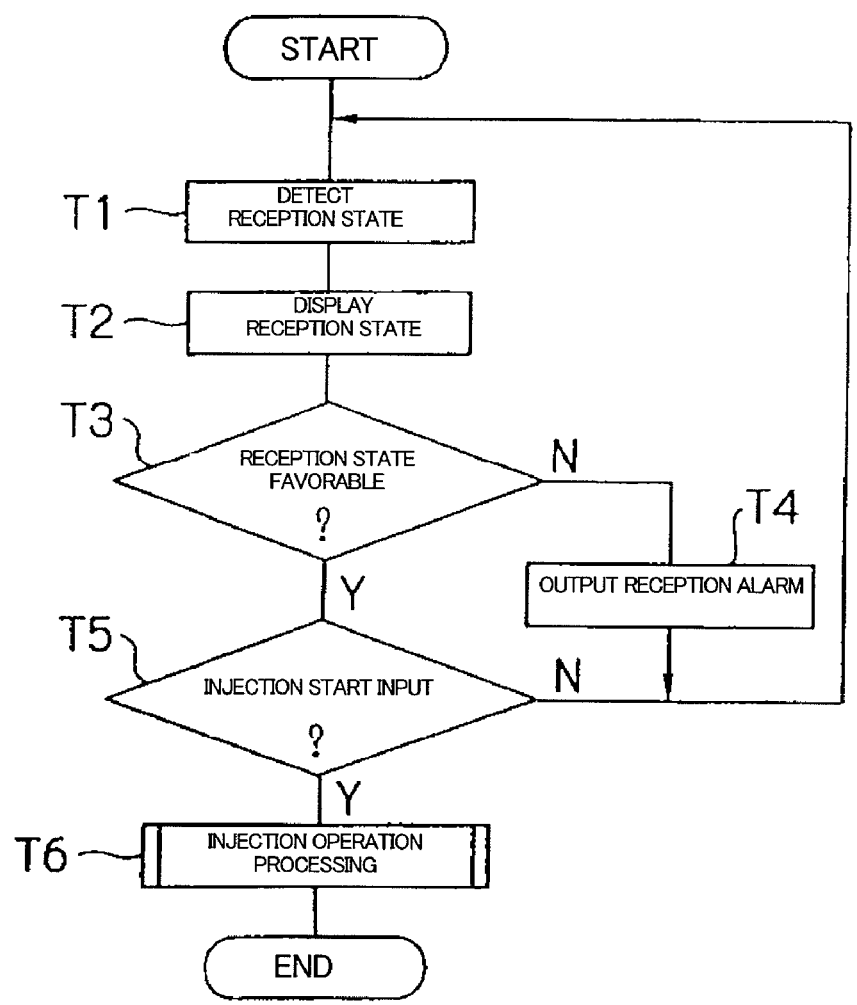

[Fig. 11]
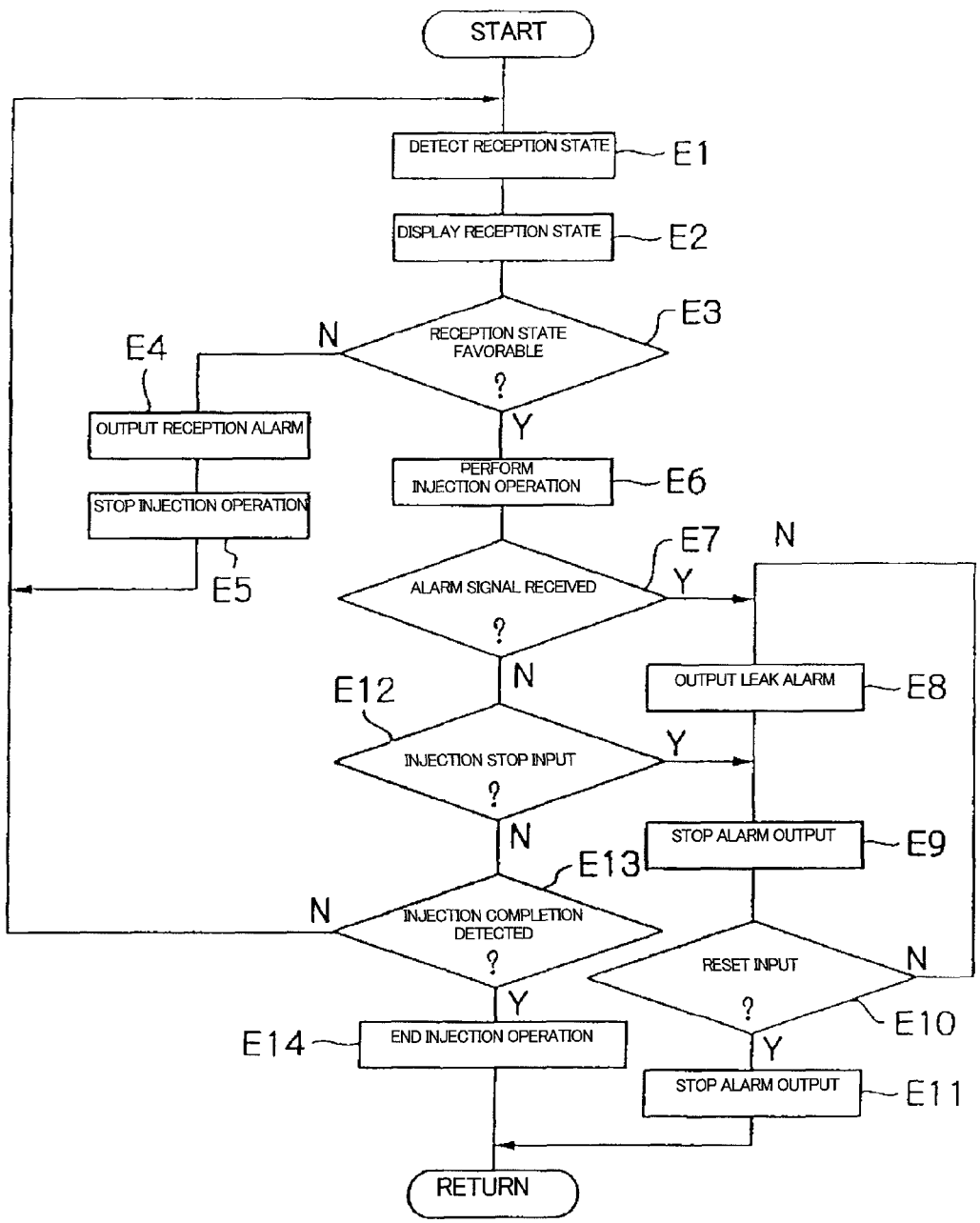

[Fig. 12]
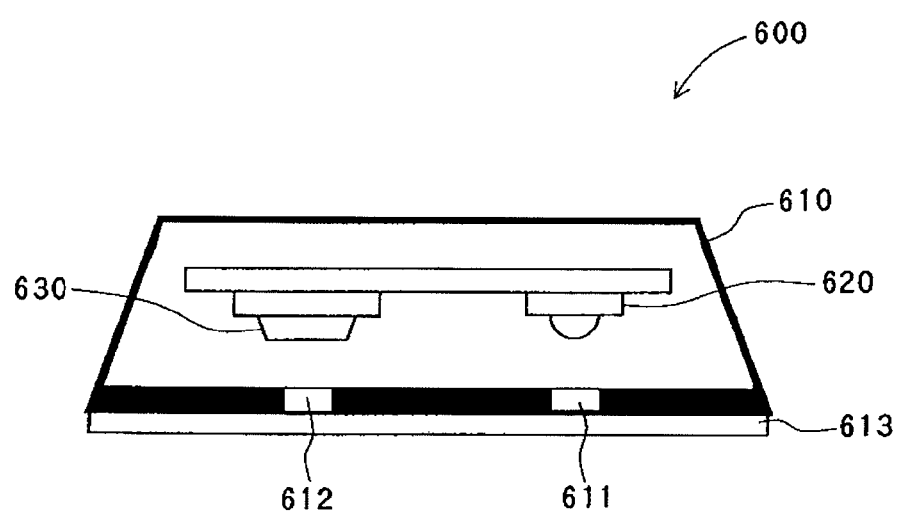

[Fig. 13]
(a)
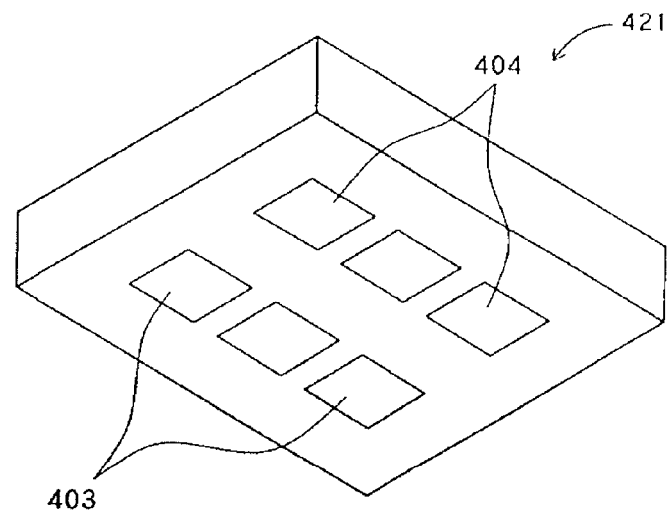
(b)
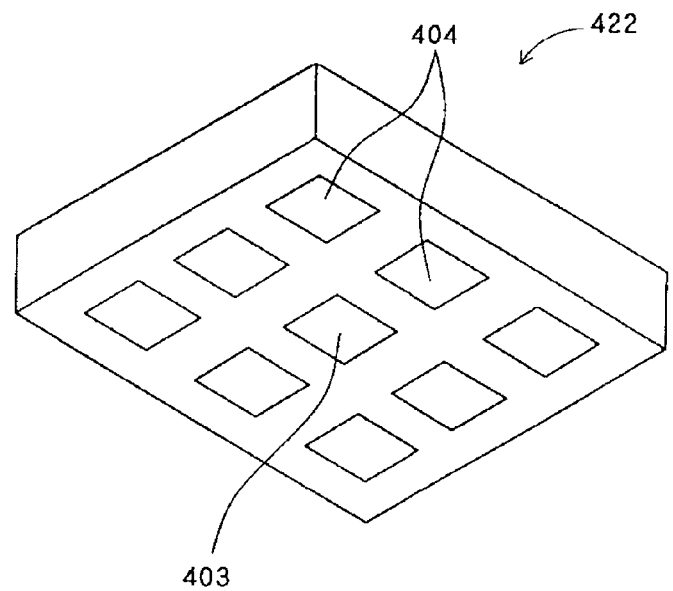

US 7,809,430 B2

LEAK DETECTING APPARATUS

This application is the U.S. National Phase under 35 U.S.C. §371 of International Application PCT/JP2005/16811, filed Sep. 13, 2005, which claims priority to Japanese Patent Application No. 2004-267062, filed Sep. 14, 2004. The International Application was published under PCT Article 21(2) in a language other than English.

TECHNICAL FIELD

The present invention relates to a leak detecting apparatus for detecting leak of a liquid injected into a blood vessel of a human body near the surface thereof through an injection needle, and more particularly, to a leak detecting apparatus for detecting leak of a liquid injected by a chemical liquid injector.

BACKGROUND ART

Presently available medical apparatuses for capturing diagnostic images of patients include CT (Computed Tomography) scanners, MRI (Magnetic Resonance Imaging) apparatuses, PET (Positron Emission Tomography) apparatuses, ultrasonic diagnostic apparatuses and the like. Angiography apparatuses, MRA (MR angiography) apparatuses and the like are currently used as medical apparatuses for capturing vascular images of patients.

When the abovementioned medical apparatuses are used, a liquid such as a contrast medium or physiological saline may be injected into a patient. Chemical liquid injectors for automatically performing the injection have been put into practical use. A liquid syringe, for example including a cylinder member and a piston member slidably inserted into the cylinder member, is mounted on such a chemical liquid injector. A syringe driving mechanism presses the piston member into the cylinder member. The cylinder member is filled with a liquid and connected to a blood vessel of a human body near the surface thereof through an extension tube and an injection needle. Thus, the liquid in the liquid syringe is injected with pressure into the blood vessel of the human body by the chemical liquid injector.

Such a chemical liquid injector automatically injects the liquid at high pressure. For example, when the injection needle deviates from the vessel to leak under skin, an operator does not easily recognize it immediately. To solve the problem, various leak detecting apparatuses have been proposed for detecting leak of a liquid injected into a blood vessel of a human body near the surface thereof through an injection needle (see, for example, patent documents 1 to 8 below).

Patent document 1: U.S. Pat. No. 6,408,204
Patent Document 2: U.S. Pat. No. 5,964,703
Patent Document 3: U.S. Pat. No. 5,947,910
Patent Document 4: U.S. Pat. No. 6,375,624
Patent Document 5: U.S. Pat. No. 5,954,668
Patent Document 6: U.S. Pat. No. 5,334,141
Patent Document 7: U.S. Pat. No. 4,647,281
Patent Document 8: U.S. Pat. No. 4,877,034

DISCLOSURE OF THE INVENTION

Subject to be Solved by the Invention

The leak detecting apparatuses in above Patent Documents 1 to 3 detect leak of a liquid based on a change in impedance at a surface of a human body. The leak detecting apparatuses in Patent Documents 4 to 7 detect leak of a liquid based on a change in temperature of a tissue of a human body. The leak detecting apparatus in Patent Document 8 detects leak of a liquid based on a change in optical characteristics of blood. However, human bodies have large individual variations, and the impedance, the temperature, and the optical characteristics are changed with physical condition, so that the above-mentioned leak detecting apparatuses cannot easily detect leak of a liquid accurately and consistently.

The present invention has been made in view of the above-mentioned problem, and it is an object thereof to provide a leak detecting apparatus which has a simple structure and has detection accuracy which is reduced only slightly by disturbance.

Means to Solve the Subject

According to a first aspect to a fifth aspect, the present invention provides a leak detecting apparatus which includes a light ray emitting means, a light ray detecting means, a first measuring means, a second measuring means, a ratio calculating means, a leak determining means, and a leak alarming means to detect leak of a liquid injected through an injection needle to a blood vessel of a human body near the surface thereof.

In the leak detecting apparatus according to the first aspect of the present invention, the light ray emitting means emits a light ray in a predetermined wavelength band containing a particular wavelength at which the reflectivity for the liquid is higher than the reflectivity for internal tissues of the human body, to the human body at a position thereof where the injection needle is inserted. The light ray detecting means detects the light ray in the wavelength band reflected inside the human body. The first measuring means measures the intensity of the detected light ray at the particular wavelength, and the second measuring means measures the average intensity of the detected light ray in the wavelength band. The ratio calculating means calculates the ratio of the intensity at the particular wavelength to the measured average intensity. The leak determining means determines the occurrence of leak when the calculated ratio is higher than a predetermined reference value. The leak alarming means outputs and notifies a leak alarm when the occurrence of leak is determined. Thus, in the leak detecting apparatus, when the liquid injected into the blood vessel from the injection needle is leaked, the leak alarm is output and notified by using the increased intensity of the light ray at the particular wavelength reflected inside the human body as compared with the average intensity in the wavelength band.

In the leak detecting apparatus according to the second aspect of the present invention, the light ray emitting means emits a light ray in a predetermined wavelength band containing a particular wavelength at which the reflectivity for the liquid is lower than the reflectivity for internal tissues of the human body. When the calculated ratio is lower than a predetermined reference value, the occurrence of leak is determined. Thus, in the leak detecting apparatus, when the liquid injected into the blood vessel from the injection needle is leaked, the leak alarm is output and notified by using the reduced intensity of the light ray at the particular wavelength reflected inside the human body as compared with the average intensity in the wavelength band.

In the leak detecting apparatus according to the third aspect of the present invention, the light ray emitting means emits a light ray containing a first particular wavelength at which the reflectivity for the liquid is higher than the reflectivity for internal tissues of the human body and a second particular wavelength at which the reflectivity for the liquid is approximately equal to the reflectivity for the internal tissues of the human body. The second measuring means measures the intensity of the detected light ray at the second particular wavelength. The ratio calculating means calculates the ratio of the intensity at the first particular wavelength to the measured intensity at the second particular wavelength. The leak determining means determines the occurrence of leak when the calculated ratio is higher than a predetermined reference value. Thus, in the leak detecting apparatus, when the liquid injected into the blood vessel from the injection needle is leaked, the leak alarm is output and notified by using the increased intensity of the light ray at the first particular wavelength reflected inside the human body as compared with the intensity at the second particular wavelength.

In the leak detecting apparatus according to the fourth aspect of the present invention, the light ray emitting means emits a light ray containing a first particular wavelength at which the reflectivity for the liquid is lower than the reflectivity for internal tissues of the human body and a second particular wavelength at which the reflectivity for the liquid is approximately equal to the reflectivity for the internal tissues of the human body. The leak determining means determines the occurrence of leak when the calculated ratio is lower than a predetermined reference value. Thus, in the leak detecting apparatus, when the liquid injected into the blood vessel from the injection needle is leaked, the leak alarm is output and notified by using the reduced intensity of the light ray at the first particular wavelength reflected inside the human body as compared with the intensity at the second particular wavelength.

In the leak detecting apparatus according to the fifth aspect of the present invention, the light ray emitting means emits a light ray containing a first particular wavelength at which the reflectivity for the liquid is higher than the reflectivity for internal tissues of the human body and a second particular wavelength at which the reflectivity for the liquid is lower than the reflectivity for the internal tissues of the human body. The leak determining means determines the occurrence of leak when the calculated ratio is higher than a predetermined reference value. Thus, in the leak detecting apparatus, when the liquid injected into the blood vessel from the injection needle is leaked, the leak alarm is output and notified by using the increased intensity of the light ray at the first particular wavelength reflected inside the human body and the reduced intensity at the second particular wavelength.

Various means referred to in the present invention may be arranged to perform their functions, and may comprise dedicated hardware for performing a predetermined function, a data processing apparatus whose predetermined function is given by a computer program, a predetermined function performed in a data processing apparatus according to a computer program, or a combination thereof.

Various components referred to in the present invention do not need to be a separate entity. A plurality of components may be constructed as one member, a single component may be constructed by a plurality of members, a certain component may be part of another component, or a certain component may have a portion overlapping a portion of another component.

EFFECT OF THE INVENTION

In the leak detecting apparatus according to the first aspect of the present invention, when the liquid injected into the blood vessel from the injection needle is leaked, the leak alarm is output and notified by using the increased intensity of the light ray at the particular wavelength reflected inside the human body as compared with the average intensity in the wavelength band, so that the leak alarm can be output and notified with high accuracy without being affected by variations in human body or physical condition.

In the leak detecting apparatus according to the second aspect of the present invention, when the liquid injected into the blood vessel from the injection needle is leaked, the leak alarm is output and notified by using the reduced intensity of the light ray at the particular wavelength reflected inside the human body as compared with the average intensity in the wavelength band, so that the leak alarm can be output and notified with high accuracy without being affected by variations in human body or physical condition.

In the leak detecting apparatus according to the third aspect of the present invention, when the liquid injected into the blood vessel from the injection needle is leaked, the leak alarm is output and notified by using the increased intensity of the light ray at the first particular wavelength reflected inside the human body as compared with the intensity at the second particular wavelength, so that the leak alarm can be output and notified with high accuracy without being affected by variations in human body or physical condition.

In the leak detecting apparatus according to the fourth aspect of the present invention, when the liquid injected into the blood vessel from the injection needle is leaked, the leak alarm is output and notified by using the reduced intensity of the light ray at the first particular wavelength reflected inside the human body as compared with the intensity at the second particular wavelength, so that the leak alarm can be output and notified with high accuracy without being affected by variations in human body or physical condition.

In the leak detecting apparatus according to the fifth aspect of the present invention, when the liquid injected into the blood vessel from the injection needle is leaked, the leak alarm is output and notified by using the increased intensity of the light ray at the first particular wavelength reflected inside the human body and the reduced intensity at the second particular wavelength, so that the leak alarm can be output and notified with high accuracy without being affected by variations in human body or physical condition.

BRIEF DESCRIPTION OF THE DRAWINGS

FIG. 1 is a schematic diagram showing the logical structure of a chemical liquid injector integral with a leak detecting apparatus according to an embodiment of the present invention.

FIG. 2 is a block diagram showing the physical structure of a diagnostic imaging system.

FIG. 3 is a perspective view showing the outer appearance of the diagnostic imaging system.

FIG. 4 is a perspective view showing the outer appearance of the chemical liquid injector.

FIG. 5 are perspective views showing how the liquid syringe is mounted on an injection head.

FIG. 6 is a sectional view showing the internal structure of a leak detecting unit.

FIG. 7 is a perspective view showing how the leak detecting unit is mounted on an arm portion of a human body.

FIG. 8 are graphs showing the detection results of infrared rays serving as light rays.

FIG. 9 is a flow chart showing the processing operation of the leak detecting unit.

FIG. 10 is a flow chart showing the main routine in the processing operation of an injection apparatus body.

FIG. 11 is a flow chart showing the sub routine of the injection operation.

FIG. 12 is a sectional view showing the internal structure of a leak detecting unit formed in an experiment.

FIG. 13 are perspective views showing modifications of the leak detecting unit.

DESCRIPTION OF REFERENCE NUMERALS

100 CHEMICAL LIQUID INJECTOR also serving as leak detecting apparatus
101 INJECTOR BODY doubling as detecting apparatus body
103 LIQUID CRYSTAL DISPLAY serving as image display means
131 WIRELESS RECEIVING UNIT serving as wireless receiving means
141 LEAK ALARMING MEANS
142 RECEPTION DETECTING MEANS
143 STATE NOTIFYING MEANS
144 RECEPTION ALARMING MEANS
146 INJECTION STOPPING MEANS
200 LIQUID SYRINGE
211 CYLINDER MEMBER
220 PISTON MEMBER
421, 422, 600 LEAK DETECTING UNIT
403 LIGHT-EMITTING DIODE corresponding to infrared ray emitting means
404, 630 PHOTOTRANSISTOR corresponding to infrared ray detecting means
409 WIRELESS TRANSMITTING UNIT serving as wireless transmitting means
411 FIRST MEASURING MEANS
412 SECOND MEASURING MEANS
413 RATIO CALCULATING MEANS
414 LEAK DETERMINING MEANS
500 ARM PORTION OF HUMAN BODY
501 BLOOD VESSEL
620 INFRARED RAY LED corresponding to infrared ray emitting means

BEST MODE FOR CARRYING THE INVENTION

Configuration of Embodiment

An embodiment of the present invention will hereinafter be described with reference to the drawings. Although the directions of forward, rearward, leftward, rightward, upward, and downward are specified as shown in the embodiment, these directions are defined for convenience to facilitate the description, and the definition does not limit any direction in manufacture or actual use of the apparatus of the present invention.

As shown in FIGS. 1 to 3, chemical liquid injection system 1000 of the embodiment according to the present invention comprises chemical liquid injector 100, liquid syringe 200, and CT scanner 300 which serves as a diagnostic imaging apparatus. The system is provided for taking diagnostic images of a patient (not shown) injected with a liquid such as a contrast medium, described later in detail.

As shown in FIGS. 2 and 3, CT scanner 300 includes diagnostic imaging unit 301 serving as a mechanism for performing imaging and imaging control unit 302 such that diagnostic imaging unit 301 and imaging control unit 302 are wire-connected through communication network 303. Diagnostic imaging unit 301 shoots a diagnostic image of a patient. Imaging control unit 302 controls the operation of diagnostic imaging unit 301.

As shown in FIG. 5, liquid syringe 200 comprises cylinder member 210 and piston member 220 wherein piston member 220 is slidably inserted into cylinder member 210. Cylinder member 210 includes cylindrical hollow body 211 which has conduit 212 formed at the closed leading end surface.

The trailing end of body 211 of cylinder member 210 is opened and piston member 220 is inserted from the opening into the interior of body 211. Cylinder member 210 has cylinder flange 213 formed in the outer circumference of the trailing end, and piston member 220 has piston flange 221 formed in the outer circumference of the trailing end.

As shown in FIG. 4, chemical liquid injector 100 of the embodiment has injection control unit 101 and injection head 110 constructed as separate components which are wire-connected through communication cable 102. Injection head 110 is attached to the top end of caster stand 111 by movable arm 112.

As shown in FIG. 5, head body 113 of injection head 110 has concave portion 114 formed in its upper surface in a semi-cylindrical shape fitting cylinder member 210 of liquid syringe 200. Cylinder holding mechanism 115 is formed in the forward section of concave portion 114 for removably holding cylinder flange 211 of liquid syringe 200.

Piston driving mechanism 116 is placed in the rearward section of concave portion 114 of injection head 110 for holding and sliding piston flange 221. Piston driving mechanism 116 removably holds and slides piston member 220 of liquid syringe 200 in the forward and rearward directions.

In chemical liquid injector 100 of the embodiment, as shown in FIG. 7, liquid syringe 200 held by injection head 110 is connected to blood vessel 501 of arm portion 500 of a human body through extension tube 211 and injection needle 212, for example. Injection needle 212 is held by adhesive pad 213 formed of a transparent sheet through which infrared rays adequately pass.

As shown in FIG. 2, piston driving mechanism 116 has driving motor 117 such as an ultrasonic motor as a driving source which is free from generation of magnetic field even in operation, and slides piston member 220 through a screw mechanism (not shown) or the like. Empty sensor 118 is contained in piston driving mechanism 116 and detects the position of slid piston flange 221 to sense the completion of liquid injection with liquid syringe 200.

Injection control unit 101 connected through communication cable 102 to injection head 110 formed as described above contains a computer unit 130 and is connected to imaging control unit 302 of CT scanner 300 through communication network 304.

As shown in FIG. 4, injection control unit 101 has operation panel 103, liquid crystal display 104 serving as a data display means, speaker unit 105 and the like, all of which are disposed on the front face of unit housing 106. Injection control unit 101 is wire-connected to controller unit 107 as a separate component through connector 108.

Chemical liquid injector 100 of the embodiment is integral with a leak detecting apparatus, and injection control unit 101 thereof also serves as the detecting apparatus body. Thus, leak detecting unit 401 is formed as a separate component from injection control unit 101 and wirelessly communicates with injection control unit 101.

For this reason, injection control unit 101 also contains wireless receiving unit 121 serving as a wireless receiving means which wirelessly communicates with leak detecting unit 401. As shown in FIG. 2, various devices such as wireless receiving unit 121 are wire-connected to computer unit 130.

Computer unit 130 is formed of a so-called one-chip microcomputer provided with hardware such as CPU (Central Processing Unit) 131, ROM (Read Only Memory) 132, RAM (Random Access Memory) 133, I/F (Interface) 134 and the like. Computer unit 130 has an appropriate computer program installed as firmware or the like in an information storage medium such as ROM 132. CPU 131 executes various types of processing in accordance with the computer program.

On the other hand, leak detecting unit 401 has unit housing 402 in a box shape as shown in FIG. 6. Unit housing 402 contains light-emitting diode 403 serving as a light emitting means and phototransistor 404 serving as a light detecting means such that they face downward.

Light-emitting diode 403 emits infrared rays as light rays in a predetermined wavelength band in a downward direction. Photodiode 404 receives the infrared rays in the wavelength band from below. More specifically, the infrared rays emitted by light-emitting diode 403 are set in the wavelength band which is reflected uniformly by the internal tissues of arm portion 500, and the wavelength band includes a particular wavelength at which infrared rays are absorbed at a high rate by a liquid such as a contrast medium and the reflectivity for a liquid such as a contrast medium is lower than the reflectivity for the internal tissues of arm portion 500.

When the liquid is not leaked inside arm portion 500, the infrared rays in the wavelength band reflected inside arm portion 500 and then detected have a substantially constant intensity as shown in FIG. 8(a). However, if the liquid is leaked inside arm portion 500, the infrared rays in the wavelength band reflected inside arm portion 500 and then detected have an intensity which is extremely reduced only at the particular wavelength as shown in FIG. 8(b).

Optical filter 406 is placed at a lower position opposite to light-emitting diode 403 and phototransistor 404. Optical filter 406 allows infrared rays only in the abovementioned wavelength band to pass therethrough. Circuit board 407 is placed in an upper portion within leak detecting unit 401. As shown in FIG. 2, light-emitting diode 403, phototransistor 404, central processing unit 408, wireless transmitting unit 409 serving as a wireless transmitting means are mounted on circuit board 407.

Central processing unit 408 is wire-connected to light-emitting diode 403, phototransistor 404, and wireless transmitting unit 409, and causes light-emitting diode 403 to continuously emit infrared rays and continuously takes the output from phototransistor 404. Central processing unit 408 is formed as a logical circuit having a predetermined structure, and has various types of hardware functioning as first measuring means 411, second measuring means 412, ratio calculating means 413, and leak determining means 414.

First measuring means 411 comprises, for example, an A/D (Analog/Digital) converter and an arithmetic processing circuit (not shown) and measures the intensity of light rays at the particular wavelength detected by phototransistor 404. Second measuring means 412 also comprises an A/D converter, an arithmetic processing circuit and the like, and measures the average intensity of the detected light rays in the wavelength band.

The intensity of light rays at the particular wavelength to be measured as described above may be the intensity of light rays only at the particular wavelength, or the average of light rays in a predetermined range of wavelengths centering on the particular wavelength, for example. The average intensity of light rays in the wavelength band may be the average of light rays in the entire wavelength band including the abovementioned particular wavelength, or the average of light rays other than a predetermined range centering on the particular wavelength in the abovementioned wavelength band, for example.

Ratio calculating means 413 and leak determining means 414 comprise a predetermined arithmetic processing circuit and the like. Ratio calculating means 413 calculates the ratio of the intensity of the measured light rays at the particular wavelength to the average intensity in the wavelength band as described above. Leak determining means 414 determines the occurrence of leak if the calculated ratio is lower than a predetermined reference value.

Central processing circuit 408 causes wireless transmitting unit 409 to continuously transmit a predetermined standby signal through radio waves when leak determining means 414 does not determine the occurrence of leak as described above. If the occurrence of leak is determined, central processing circuit 408 causes wireless transmitting unit 409 to wirelessly transmit a predetermined alarm signal.

In chemical liquid injector 100 of the embodiment, microprocessor 130 integrates and controls the respective components in accordance with the computer program as described above to have various means logically, as various functions, such as leak alarming means 141, reception detecting means 142, state notifying means 143, reception alarming means 144, and injection stopping means 146, as shown in FIG. 1.

Leak alarming means 141 corresponds to the function of microprocessor 130 which controls the operation of speaker unit 105 and liquid crystal display 104 in accordance with the computer program. When the standby signal wirelessly received by wireless receiving unit 121 is switched to the alarm signal, leak alarming means 141 outputs and notifies the leak alarm with sound from speaker unit 105 and an image displayed on liquid crystal display 104.

Reception detecting means 142 corresponds to the function of microprocessor 130 which detects the data about the operation state of wireless receiving unit 121, and detects the reception state of a radio signal. State notifying means 143 corresponds to the function of microprocessor 130 which controls the operation of liquid crystal display 104, and outputs and notifies the reception state detected by reception detecting means 142 with an image displayed on liquid crystal display 104 or the like.

Reception alarming means 144 corresponds to the function of microprocessor 130 which controls the operation of speaker unit 105 and liquid crystal display 104, and outputs and notifies a reception alarm with sound output from speaker unit 105 and an image displayed on liquid crystal display 104 if the reception state detected by reception detecting means 142 is reduced below than a predetermined state.

Injection stopping means 146 corresponds to the function of microprocessor 130 which controls the operation of driving motor 117 of piston driving mechanism 116, and stops driving motor 117 to stop the injection of the liquid when at least one of the leak alarm and the reception alarm is output.

Although the abovementioned various means 141 to 146 of chemical liquid injector 100 are accomplished by pieces of hardware such as speaker unit 105 as required, they are mainly implemented by microprocessor 130 functioning in accordance with the installed computer program.

Such a computer program is described to cause microprocessor 130 to perform processing operations including the output and notification of the leak alarm from speaker unit 105 and on liquid crystal display 104 when wireless receiving unit 121 wirelessly receives the alarm signal, the stop of driving motor 117 in association with the output of the leak alarm, the detection of the reception state of wireless receiving unit 121, the output and notification of the reception state on liquid crystal display 104, the output and notification of the reception alarm from speaker unit 105 and on liquid crystal display 104 when the reception state is reduced than the predetermined state, and the stop of driving motor 117 in association with the output of the reception alarm.

For simplify the representation, control unit 302 and the whole chemical liquid injector 100 are placed near diagnostic imaging unit 301 of CT scanner 300 in FIG. 3. However, for practical use in a medical facility, only injection head 110 is placed near diagnostic imaging unit 301, and control unit 302 and injection control unit 101 are disposed in a different room.

Operation of the Embodiment

When chemical liquid injector 100 of the embodiment is used in the abovementioned arrangement, for example, an operator connects injection needle 212 through extension tube 211 to liquid syringe 200 filled with a liquid such as a contrast medium, and inserts injection needle 212 into blood vessel 501 of arm portion 500 of a patient on diagnostic imaging unit 301 of CT scanner 300 and holds injection needle 212 with adhesive pad 213 as shown in FIG. 7.

Next, the operator places leak detecting unit 401 on the surface of adhesive pad 213 with a restraint belt (not shown) or the like, and mounts liquid syringe 200 on injection head 110 of chemical liquid injector 100. With this state, the operator turns on each power switch (not shown) of leak detecting unit 401 and injection control unit 101, and for example, sets an operation mode for using leak detecting unit 401 on injection control unit 101 through a predetermined operation.

Then, as shown in FIG. 9, leak detecting unit 401 emits infrared rays in the predetermined wavelength band from light-emitting diode 403 toward the position where injection needle 212 is connected to blood vessel 501 of arm portion 500 and detects the infrared rays with phototransistor 404 (step S1). The intensity of the detected infrared rays at the particular wavelength in the predetermined wavelength band is measured (step S2), and the average strength in the wavelength band is measured (step S3). The ratio of the intensity of the light rays at the particular wavelength to the average intensity in the wavelength band thus measured is calculated (step S4), and the calculated ratio is compared with the predetermined reference value (step S5).

If the ratio is not lower than the reference value, the occurrence of leak of the liquid is not determined, and leak detecting unit 401 wirelessly transmits a standby signal representing "no leak" to injection control unit 101 (step S6). On the other hand, if the abovementioned ratio is lower than the reference value, the occurrence of leak of the liquid is determined (step S7), and leak detecting unit 401 wirelessly transmits an alarm signal representing "occurrence of leak" to injection control unit 101 (step S8).

Next, the method of detecting leak in chemical liquid injector 100 of the embodiment will hereinafter be described in brief. The infrared rays emitted by light-emitting diode 403 of leak detecting unit 401 are set in the wavelength band reflected uniformly by the internal tissues of arm portion 500 as described above. The wavelength band includes the particular wavelength at which the reflectivity for a predetermined liquid such as a contrast medium is lower than the reflectivity for the internal tissues of arm portion 500.

When the liquid is not leaked inside arm portion 500, the infrared rays in the wavelength band reflected inside arm portion 500 and then detected have a substantially constant intensity as shown in FIG. 8(a). However, if the liquid is leaked inside arm portion 500, the infrared rays in the wavelength band reflected inside arm portion 500 and then detected have an intensity which is extremely reduced only at the particular wavelength as shown in FIG. 8(b).

The ratio of the intensity at the particular wavelength to the average intensity in the wavelength band is approximately "1" when no liquid is leaked inside arm portion 500, but is extremely reduced below "1" when the liquid is leaked. Thus, in chemical liquid injector 100 of the embodiment, the abovementioned ratio is compared with the reference value such as "0.8" to determine whether or not the liquid is leaked with high accuracy.

As shown in FIG. 10, injection control unit 101 continuously detects the reception state of radio waves in the operation state where leak detecting unit 401 is used (step T1), and outputs by displaying the reception state in real time with a bar graph or the like on liquid crystal display 104 (step T2).

With this operation, the operator can check the reception state of radio waves from leak detecting unit 401 in real time while operating injection control unit 101, and performs the adjustment of injection control unit 101 or the position of leak detecting unit 401 if the reception state is not favorable.

When the detected reception state is reduced below the predetermined state as described above (step T3), injection control unit 101 outputs a reception alarm such as "Radio wave reception impossible. Check communication state" with display on liquid crystal display 104 and sound form speaker unit 105 (step T4).

Since injection control unit 101 does not accept any entry operation to start injection before the reception state from leak detecting unit 401 is changed to a favorable state (steps T3 to T5), it starts the injection operation of the liquid only when the reception state is favorable (step T6).

When injection control unit 101 receives entry operation to start the injection of the liquid (steps T5 and T6), it continuously detects the reception state of radio waves, and outputs it by displaying on liquid crystal display 104 in real time as shown in FIG. 11 (steps E1 and E2).

When the detected reception state is reduced below the predetermined state, it outputs and notifies the reception alarm on liquid crystal display 104 and from speaker unit 105 (steps E3 and E4), and performs the injection operation of the liquid only when the reception state is favorable (steps E3 to E6).

Injection control unit 101 performs the injection operation in the favorable reception state (step E6), and if the wirelessly received standby signal is changed into the alarm signal (step E7), it outputs a leak alarm such as "Removal of injection needle detected. Check injection needle" with display on liquid crystal display 104 and sound from speaker unit 105 (step E8).

Since the injection operation of the liquid is stopped in this case (step E9), the liquid injection is not continued while injection needle 212 comes off blood vessel 501. In addition, the abovementioned output of the leak alarm is continued until predetermined reset operation is input on injection control unit 101 (steps E10 and E11), the operator recognizes the leak alarm without fail.

In chemical liquid injector 100 of the embodiment, after the recognition of the leak alarm, the operator appropriately inserts injection needle 212 into blood vessel 501 and then makes entry operation to start the injection of the liquid on operation panel 103. In response thereto, the liquid injection can be started again (steps T5 and 6).

When the operator makes entry operation to stop the injection (step E12), injection control unit 101 stops the injection of the liquid (step E9). When empty sensor 118 senses the completion of the injection of the liquid (step E13), injection control unit 101 ends the injection of the liquid (step E14).

Effect of the Embodiment

Chemical liquid injector 100 of the embodiment emits the infrared rays in the predetermined wavelength band including the particular wavelength at which the reflectivity for the liquid is lower than the reflectivity for the internal tissues within arm portion 500 as described above, and determines the occurrence of leak when the ratio of the intensity of the infrared rays at the particular wavelength to the average intensity in the wavelength band reflected inside arm portion 500 is reduced below the reference value.

For example, when the intensity of infrared rays reflected inside arm portion 500 or the like is changed by variations in human body or physical condition, that change affects the overall reflection intensity in the wavelength band but has substantially no effects on the ratio of the intensity at the particular wavelength to the average intensity in the wavelength band. Thus, chemical liquid injector 100 of the embodiment can determine the leak of the liquid with high accuracy to output and notify the alarm without being affected by variations in human body or physical condition, and the operator can immediately recognize removal of injection needle 212 from blood vessel 501 of the patient and takes measures.

In chemical liquid injector 100 of the embodiment, if the removal of injection needle 212 is detected as described above, the injection of the liquid can be automatically stopped to automatically prevent the liquid injection from being continued while injection needle 212 comes off blood vessel 501. In addition, light-emitting diode 403 emits the infrared rays in the wavelength band reflected favorably inside arm portion 500, and optical filter 406 allows only the infrared rays in the wavelength band to pass therethrough to phototransistor 404, thereby making it possible to prevent the malfunction of detection of ambient light noise by phototransistor 404.

In chemical liquid injector 100 of the embodiment, leak detecting unit 401 including light-emitting diode 403, phototransistor 404, wireless transmitting unit 409 and the like is formed separately from injection control unit 101 including wireless receiving unit 121, liquid crystal display 104, speaker unit 105 and the like.

When leak detecting unit 401 detects the leak of the liquid, injection control unit 101 outputs and notifies the leak alarm through wireless communication. This allows leak detecting unit 401 directly mounted on the human body to be reduced in size and weight to facilitate handling, and the leak alarm can be recognized without fail by the operator who is located away from leak detecting unit 401 and manually operates injection control unit 101.

Injection control unit 101 continuously detects the reception state of the radio signal from leak detecting unit 401 and outputs the reception state in real time. Thus, the operator can always know the communication state between leak detecting unit 401 and injection control unit 101, and if the communication state is not favorable, the operator can deal with that before the injection operation is performed.

Since injection control unit 101 outputs and notifies the reception alarm when the detected reception state is reduced below the predetermined state, it is possible to prevent the situation in which the alarm signal cannot be wirelessly received due to poor communication and thus the leak alarm is not output. In addition, the liquid injection is stopped when at least one of the leak alarm and the reception alarm is output, so that it is possible not only to automatically prevent the continuous liquid injection while injection needle 212 is removed from blood vessel 501, but also to prevent the continuous liquid injection while the alarm signal cannot be wirelessly received.

The inventors have experimentally checked whether or not a contrast medium leaked in a human body can be detected with infrared rays. In the experiment, first, a light source capable of emitting light rays at wavelengths of approximately 450 nm to 1350 nm was prepared, and the light source was placed at one end of a light-shield container and a spectrometer was disposed at the other end. Then, the intensity of light rays was measured by the spectrometer for each wavelength in the state where the container was filled with air as a reference, the state where the container was filled with water substituting for a human body, and the state where the container was filled with a typical contrast medium for CT. It was revealed that the contrast medium adequately absorbed the light rays at a wavelength near 950 nm as compared with the air and water.

Since a human body adequately transmits infrared rays at wavelengths of approximately 800 to 1000 nm, the inventors performed a second experiment by using an infrared LED (Light-Emitting Diode) with a peak wavelength of 950 nm as a light source. In the second experiment, a first chicken piece was placed at the bottom of a light-shield container and the container was sealed by a first acrylic plate. A second acrylic plate was disposed in parallel with the first acrylic plate such that they are spaced from each other, and a second chicken piece was placed on the surface of the second acrylic plate. A model of a human body was formed in this manner (not shown).

An infrared LED with a peak wavelength of 950 nm and a spectrometer were placed in parallel to form a trial detecting unit (not shown) similar to leak detecting unit 401 of the embodiment. The trial detecting unit was placed in intimate contact with the surface of the second chicken piece of the human body model. Then, the intensity of the infrared rays was measured by the spectrometer for each wavelength in the state where the human body model was filled with air, the state where the model was filled with water, and the state where the model was filled a contrast medium. It was revealed that the detected intensity of the contrast medium was extremely reduced near at a wavelength of 950 nm as compared with the air and water.

In other words, in leak detecting unit 401 of the embodiment, the infrared LED with a peak wavelength of 950 nm was used as light-emitting diode 401 and phototransistor 404 detects the intensity of infrared rays at the wavelength of 950 nm, for example, thereby allowing favorable determination of leak of the contrast medium. Since the infrared LED with a peak wavelength of 950 nm as described above is commercially available as a product, such a product can be used to implement leak detecting unit 401 of the embodiment with favorable productivity.

After seeing the foregoing results, the inventors manufactured leak detecting unit 600 by way of trial as shown in FIG. 12 to perform a third experiment. Leak detecting unit 600 has unit housing 610 in a box shape. Unit housing 610 contains infrared LED 620 with a peak output wavelength of 950 nm and phototransistor 630 with a peak detection wavelength of 880 nm such that they face downward.

Unit housing 610 has circular opening holes 611 and 612 at positions opposite to infrared LED 620 and phototransistor 630 at the bottom plate, respectively. Transparent sheet 613 made of resin such as PET (Polyethylene Terephthalate) and PS (Poly-Styrene) is placed over the entire bottom surface.

Enlarging and reducing opening hole 612 opposite to phototransistor 630 increases and reduces the amount of received light, but the effects of noise due to the surface state or the like of the human body are also increased and reduced, so that an extremely large or small size of opening hole 612 does not provide excellent detection sensitivity. The inventors performed an experiment to see the detection sensitivity with diameters of opening hole 612 of 1.0 mm, 1.5 mm, and 3.0 mm. The resulting S/N ratios (Signal-to-Noise ratio) were 1.8, 5.0, and 3.0, with the maximum level at the diameter of 1.5 mm.

In the environment where leak detecting unit 600 as described above is used, a fluorescent lamp is typically used as illumination. The inventors investigated spectral characteristics of a typical white fluorescent lamp and found that the typical white fluorescent lamp hardly output light rays at wavelengths of 800 nm or longer. In other words, it was shown that leak detecting unit 600 for detecting liquid leak at a wavelength of 950 nm as described above can favorably function without being affected by outside light in a typical environment where the white fluorescent lamp is used as illumination.

Modifications of the Embodiment

The present invention is not in any way limited to the abovementioned embodiment, but various changes and modifications may be made therein without departing from the scope of the invention. For example, in the above embodiment, the leak detecting apparatus is formed integrally with chemical liquid injector 100. The leak detecting apparatus may be formed separately from chemical liquid injector 100.

Since the injection of the liquid must be stopped immediately after the leak of the liquid is detected as described above, the leak detecting apparatus formed integrally with chemical liquid injector 100 is effective. Thus, if the leak detecting apparatus is formed separately from chemical liquid injector 100, chemical liquid injector preferably stops the injection operation in association with output of an alarm from the leak detecting apparatus.

In the above embodiment, chemical liquid injector 100 outputs and notifies the leak alarm and the reception alarm. For example, the alarm may be transmitted as data to control unit 302 of CT scanner 300 and output and notified on liquid crystal display 304. Since control unit 302 is placed in a different room from diagnostic imaging unit 301 as described above, notifying diagnostic imaging unit 301 of the alarm is effective.

In the above embodiment, only chemical liquid injector 100 stops the injection operation in response to the leak alarm. For example, CT scanner 300 may also stop the imaging operation in association with the stop of the operation of chemical liquid injector 100 described above. In this case, chemical liquid injector 100 may directly transmit the alarm signal of leak detecting unit 401 as data to CT scanner 300, or may indirectly transfer it as data via injection control unit 101.

The above embodiment assumes that chemical liquid injector 100 is used near CT scanner 300, but it may be used near a CT scanner, a PET apparatus, an angiography apparatus, an MRA apparatus, an ultrasonic diagnostic apparatus, or the like. In the above embodiment, leak detecting unit 401 and injection control unit 101 wirelessly communicate with each other through radio signals. The communication method may be realized with wireless communication of ultrasonic signals, wireless communication of optical signals, wire communication of electric signals, wire communication of optical signals, or the like.

In the above embodiment, one light-emitting diode 403 and one phototransistor 404 are mounted on leak detecting unit 401. Alternatively, it is possible to leak detecting unit 421 which includes a plurality of light-emitting diodes 403 and a plurality of phototransistors 404 arranged therein as shown in FIG. 13(a), or leak detecting unit 422 which includes a plurality of phototransistors 404 around one light-emitting diode 403 arranged therein as shown in FIG. 13(b). Since such a leak detecting apparatus can detect leak of a liquid at a plurality of positions, the leak of the liquid can be detected more satisfactorily.

In the above embodiment, chemical liquid injector 100 causes leak alarming means 141 to output and notify only the leak alarm with an image displayed on liquid crystal display 104 or the like. For example, a graph displaying means (not shown) may be used to output and display a graph of distribution of intensity as shown in FIGS. 8(a) and 8(b) on liquid crystal display 104.

In the above embodiment, the only one particular wavelength is contained in the predetermined wavelength band of the infrared rays, but a plurality of particular wavelengths may be used. In this case, since the intensity can be measured for each of the plurality of particular wavelengths and the ratio can be calculated for each of the plurality of intensities, the occurrence of leak may be determined when all of the plurality of ratios are higher than a reference value, for example. The occurrence of leak is determined with the plurality of particular wavelengths in this case, so that the occurrence of false detection can be reduced to improve the accuracy of detection.

A failure to detect liquid leak may be prevented by determining the occurrence of leak if one of the plurality of ratios is higher than the reference value. In addition, both of the false detection and the failure to detect liquid leak may be prevented favorably by determining the occurrence of leak if a predetermined number of the plurality of ratios are higher than the reference value or if the majority of the plurality of ratios are higher than the reference value. When the predetermined wavelength band of the infrared rays contains the plurality of particular wavelengths as described above, the plurality of calculated ratios may be individually compared with specific reference values to improve the accuracy of determination of occurrence of leak.

In the above embodiment, light-emitting diode 403 emits the infrared rays in the predetermined wavelength band containing the particular wavelength at which the reflectivity for the liquid is lower than the reflectivity for the internal tissues of arm portion 500, and the occurrence of leak is determined if the intensity of the infrared rays at the particular wavelength reflected inside arm portion 500 is lower than the average intensity in the wavelength band.

Alternatively, light-emitting diode 403 emits infrared rays in a wavelength band containing a particular wavelength at which the reflectivity for the liquid is higher than the reflectivity for the internal tissues of arm portion 500, and the occurrence of leak is determined if the ratio of the intensity of the infrared rays at the particular wavelength to the average intensity in the wavelength band reflected inside arm portion 500 is higher than a reference value.

It is also possible that light-emitting diode 403 emits infrared rays containing a first particular wavelength at which the reflectivity for the liquid is higher than the reflectivity for the internal tissues of arm portion 500 and a second particular wavelength at which the reflectivity for the liquid is approximately equal to the reflectivity for the internal tissues, and the occurrence of leak is determined if the reflected intensity at the first particular wavelength to the reflected intensity at the second particular wavelength is higher than a reference vale.

It is also possible that light-emitting diode 403 emits infrared rays containing a first particular wavelength at which the reflectivity for the liquid is lower than the reflectivity for the internal tissues of arm portion 500 and a second particular wavelength at which the reflectivity for the liquid is approximately equal to the reflectivity for the internal tissues, and the occurrence of leak is determined if the reflected intensity at the first particular wavelength to the reflected intensity at the second particular wavelength is lower than a reference vale.

It is also possible that light-emitting diode 403 emits infrared rays containing a first particular wavelength at which the reflectivity for the liquid is higher than the reflectivity for the internal tissues of arm portion 500 and a second particular wavelength at which the reflectivity for the liquid is lower than the reflectivity for the internal tissues, and the occurrence of leak is determined if the reflected intensity at the first particular wavelength to the reflected intensity at the second particular wavelength is higher than a reference vale.

In the structure in which the wavelength band contains the first and second particular wavelengths as described above, it is possible that only the first particular wavelength is realized by a plurality of wavelengths, and the ratios of the reflected intensities at the plurality of first particular wavelengths to the reflected intensity at the second particular wavelength are individually compared with a plurality of reference values. It is also possible that only the second particular wavelength is realized by a plurality of wavelengths, and the ratios of the reflected intensity at the first particular wavelength to the reflected intensities at the plurality of second particular wavelengths are individually compared with a plurality of reference values. Alternatively, each of the first and second particular wavelengths may be realized by a plurality of wavelengths, and the ratios of the reflected intensities at the plurality of first wavelengths to the reflected intensities at the plurality of second particular wavelengths may be individually compared with a plurality of reference values.

In the above embodiment, when the leak of the liquid is detected, chemical liquid injector 100 stops piston driving mechanism 116 to discontinue the liquid injection. For example, the leak detecting apparatus may include a standalone tube blocking means (not shown) for blocking extension tube 211 when leak of the liquid is detected.

Such a tube blocking means is formed as a standalone unit structure which is mounted on extension tube 211, and performs wireless and wire communication with leak detecting unit 401 and the detecting apparatus body, for example. The tube blocking means also includes a mechanism for opening or closing extension tube 211 with a driving source such as a solenoid, and blocks extension tube 211 when the leak of the liquid is detected. In such a leak detecting apparatus, extension tube 211 is blocked independently when the liquid leak is detected, so that the liquid injection can be stopped automatically even when chemical liquid injector 100 does not operate in association with the leak detecting apparatus, for example.

In the above embodiment, microprocessor 130 functions in accordance with the installed computer program to logically realize various means 141 to 146 of injection control unit 101. For example, at leas some of various means 141 to 144 may be formed by hardware such as a dedicated logical circuit.

In contrast, in the above embodiment, various means 411 to 414 of leak detecting unit 401 are formed by the predetermined hardware, but various means 411 to 414 may be logically realized by a microprocessor which functions in accordance with an installed computer program, for example.

In the above embodiment, one liquid syringe 200 is mounted in one concave portion 114 of chemical liquid injector 100, but a plurality of liquid syringes 200 may be mounted in a plurality of concave portions of the injection head (not shown). In the above embodiment, liquid syringe 200 is directly mounted on chemical liquid injector 100. Since liquid syringes 200 of various sizes are commercially available, it is possible that only liquid syringe 200 of the maximum size is directly mounted on chemical liquid injector 100 and liquid syringes 200 of the various sizes other than the maximum size are mounted on chemical liquid injector 100 via dedicated cylinder adapters (not shown).

The invention claimed is:

1. A leak detecting apparatus which detects leak of a liquid injected through an injection needle into a blood vessel of a human body near a surface thereof, comprising:
    at least one light ray emitting means for emitting a light ray in a predetermined wavelength band containing at least one particular wavelength at which the reflectivity for the liquid is lower than the reflectivity for internal tissues of the human body, to the human body at a position thereof where the injection needle is inserted;
    at least one light ray detecting means for detecting the light ray in the wavelength band reflected inside the human body;
    first measuring means for measuring the intensity of the detected light ray at the particular wavelength;
    second measuring means for measuring the average intensity of the detected light ray in the wavelength band;
    ratio calculating means for calculating the ratio of the intensity at the particular wavelength to the measured average intensity;
    leak determining means for determining occurrence of leak when the calculated ratio is lower than a predetermined reference value; and
    leak alarming means for outputting and notifying a leak alarm when the occurrence of leak is determined.

2. The leak detecting apparatus according to claim 1, further comprising a leak detecting unit which comprises at least the light ray emitting means and the light ray detecting means; and
    a detecting apparatus body formed separately from the leak detecting unit and comprising at least the leak alarming means,
    wherein the leak detecting unit comprises wireless transmitting means for transmitting a wireless signal, and the detecting apparatus body comprises wireless receiving means for receiving the wireless signal.

3. The leak detecting apparatus according to claim 1, further comprises a plurality of the light ray emitting means and/or a plurality of the light ray detecting means.

4. The leak detecting apparatus according to claim 1, further comprising an extension tube connected to the injection needle for flowing the liquid; and
    tube blocking means for blocking the extension tube when the difference exceeds the allowable range.

5. A chemical liquid injector for inserting a piston member with pressure into a cylinder member filled with a liquid in a liquid syringe connected to a human body through an injection needle and an extension tube, comprising:
    the leak detecting apparatus according to claim 1; and
    injection stopping means for stopping injection of the liquid when the leak detecting apparatus outputs and notifies the leak alarm.

6. The leak detecting apparatus according to claim 1, wherein the light ray emitting means emits the light ray at a plurality of the particular wavelengths,
   the first measuring means measures the intensity for each of the plurality of particular wavelengths, and
   the ratio calculating means calculates the ratio for each of the plurality of intensities.

7. The leak detecting apparatus according to claim 6, wherein the leak determining means determines occurrence of leak when at least one of the plurality of ratios is lower than the predetermined reference value.

8. The leak detecting apparatus according to claim 7, wherein the leak determining means individually compares the plurality of ratios with the predetermined reference values specific to the ratios.

* * * * *